United States Patent [19]

Stalker

[11] Patent Number: 4,810,648

[45] Date of Patent: Mar. 7, 1989

[54] HALOARYLNITRILE DEGRADING GENE, ITS USE, AND CELLS CONTAINING THE GENE

[75] Inventor: David M. Stalker, Davis, Calif.

[73] Assignee: Rhone Poulenc Agrochimie, Lyon, France

[21] Appl. No.: 71,146

[22] Filed: Jul. 8, 1987

Related U.S. Application Data

[63] Continuation-in-part of Ser. No. 44, Jan. 5, 1987, which is a continuation-in-part of Ser. No. 845,662, Mar. 28, 1986, abandoned, which is a continuation-in-part of Ser. No. 817,226, Jan. 8, 1986, abandoned.

[51] Int. Cl.$^4$ .................. C12N 9/06; C12N 5/00; A01H 1/00
[52] U.S. Cl. .................. 435/191; 435/240.1; 435/172.3; 435/240.49; 435/317.1; 435/320; 935/29; 536/27; 800/1; 47/58
[58] Field of Search ............ 435/68, 70, 71, 220, 435/240.1, 317, 172.3, 191, 240.25, 240.45, 240.47, 240.48, 240.49, 240.5; 530/825, 350; 536/27; 800/1; 47/58; 935/12, 14, 29

[56] References Cited

U.S. PATENT DOCUMENTS 4,438,032  3/1984  Golde et al.

OTHER PUBLICATIONS

Hsu et al. (1976) Can. J. Microbiol. (abstr.) 22: 537–543.
Harper et al. (1985) Int. J. Biochem. 165: 677–683.
Harper et al. (1977a) Bioch. J. 167: 685–692.
Harper et al. (1977 b) Bioch. J. 165: 309–319.
Thinman et al. (1984) Arch. Bioch. Biophys. 105: 133–141.
Comai et al. (1984) Crop Protection 3: 399–408.
SCIENCE (Washington DC, U.S.A.) vol. 233, issued Jul. 25, 1986, (Shah et al), "Engineering Herbicide Tolerance in Transgenic Plants", see p. 478.
SCIENCE (Washington, DC, U.S.A.), vol. 221, issued Jul. 22, 1983, (Comai et al), "An Altered aroA Gene Product Confers Resistance to the Herbicide Glypnosate", see p. 370.
Chemical Abstracts, vol. 103, No. 11, issued Sept. 16, 1985 (Columbus, Ohio, USA), Harper "Characterization of a Nitrilase From Nocardia sp. (Rhodochrous group) N.C.I.B. 11215, using p-hydroxybenzonitrile as sole carbon source", see p. 271, col. 2, the abstract No. 83953g, International Journal Biochemistry 1985, 17(6), 677–683 (ENG).
Chemical Abstracts, vol. 102, No. 25, issued Jun. 24, 1985 (Columbus, Ohio, USA), Yanase, "Metabolism of Nitriles in Pseudomonas sp", see p. 343, col. 2 p. 344, col. 1, the abstract No. 21809a, Journal Fermentation Technolgy 1985, 63(2), 193–198 (ENG).
Chemical Abstracts, vol. 102, No. 17, issued Apr. 19, 1985 (Columbus, Ohio, USA), Stalker, "Impact of Genetic Engineering on Crop Protection", see p. 329, col. 1, the abstract No. 14608b, Crop Protection 1984, 3(4), 399–408 (ENG).
Journal of Cellular Biochemistry (New York, New York, (USA), vol. Supplement 10C, issued May, 1986, (Stalker et al), "Strategies Utilizing Bacterial Genes As Herbicide Resistance Determinants in Plants", see p. 11.
Journal of Cellular Biochemistry (New York, New York, USA) vol. Supplement 10C, issued May, 1986, (Chaleff et al), "Developing Plant Varieties Resistant to Sulfonylurea Herbicides", see p. 10.

Primary Examiner—Thomas G. Wiseman
Assistant Examiner—Stephannie Seidman
Attorney, Agent, or Firm—Morgan & Finnegan

[57] ABSTRACT

Nitrilase enzymes specific for the hyrdolsis of the nitrile group of bromoxynil, nucleotide sequences encoding for such enzymes, and transformed cells in which the nitrilase expression if foreign are provided. The transformed cells are capable of expressing the nitrilase enzyme to provide detoxification of an environment and protect bromoxynil-sensitive cells from its cytotoxic effect. Particularly, plants are developed which are resistant to bromoxynil.

E. coli MM294 strain (pBrx5) was deposited at the A.T.C.C. on Jan. 22, 1986 and given Accession no. 53435.

E. coli MM294 strain (pBrx11) was deposited at the A.T.C.C. on June 18, 1987 and given Accession no. 67441.

E. coli MM294 strain (pBrx23) was deposited at the A.T.C.C. on June 18, 1987 and given Accession no. 67442.

25 Claims, No Drawings

HALOARYLNITRILE DEGRADING GENE, ITS USE, AND CELLS CONTAINING THE GENE

CROSS-REFERENCE TO RELATED APPLICATIONS

This application is a Continuation-in-part of international application Serial No. PCT/US87/00044, filed Jan. 5, 1987 which is a Continuation-in-part of application Ser. No. 845,662 abandoned, filed Mar. 28, 1986 which is a Continuation-in-part of application Ser. No. 817,226, filed Jan. 8, 1986, abandoned, which incorporates both disclosures herein by reference.

BACKGROUND OF THE INVENTION

1. Field of the Invention

The opportunity to provide novel genetic capabilities to microorganisms and cells of higher organisms has opened up broad avenues to new capabilities. In one arena is the concern with various agents that are utilized for their cytotoxic effect. For example, many compounds used in agriculture are directed to the killing of pests, weeds, or the like. In many cases, these compounds can have a relatively long residence time or extended residue.

In many situations, one wishes to distinguish between species which are to be retained and species which are to be killed. For example, it is frequently desirable to selectively kill weeds while having minimal adverse effect on crops. For the most part, many of the broad spectrum herbicides have a significant adverse effect on the crop, so that their use is primarily limited to pre-emergent use or careful postemergent application.

It is therefore of great interest to be able to modify viable cells to make them resistant to stresses such as cytotoxic agents.

DESCRIPTION OF THE RELEVANT LITERATURE

U.S. Pat. No. 4,535,060 describes the use of a bacterial aroA gene to impart glyphosate resistance to glyphosate susceptible cells. Hsu and Camper, *Can. J. Microbiol.* (1976) 22:537–543, describe isolation of ioxynil degraders from soil-enrichment cultures. Hsu and Clemson, *Dissert. Abstr. Intrn.* B36 (1976) No. 8, 3708, describe microbial degradation of a family of herbicides of 3,5-dihalogeno-4-hydroxybenzonitriles. Ingram and Pullin, *Pestic. Sci.* (1974) 5:287–291 describes the persistence of bromoxynil in three soil types. Smith, *Abstr. Meeting Weed Soc. Am.* (1971), pp. 16–17 describes the degradation of bromoxynil in Regina heavy clay. Smith and Fletcher, *Hort. Res.* (1964), 4:60–62, report on 3,5-dihalogeno-4-hydroxybenzonitriles and soil microorganisms.

SUMMARY OF THE INVENTION

Nitrilases, nucleic acid sequences encoding such nitrilases, constructs containing the genes coding such nitrilases under the transcriptional and translational regulatory control of regulatory genes recognized by a desired host to which the nitrilase genes are foreign, host cells containing such constructs, and organisms and organism parts or products containing such constructs are provided. The bromoxynil- and/or ioxynil-specific nitrilases find use for detoxifying habitats containing bromoxynil and related herbicides and protecting host cells from the cytotoxic effect of such herbicides. The constructs find use in distinguishing between host cells containing the construct and host cells lacking such construct.

DESCRIPTION OF THE SPECIFIC EMBODIMENTS

In accordance with the subject invention, novel DNA sequences, constructs, transformed cells, plants, and peptides are provided relating to hydrolysis of halogenated hydroxybenzonitriles, particularly 3,5-dibromo- or 3,5-diiodo-4- hydroxybenzonitrile. The invention concerns the production of an enzyme capable of hydrolyzing the nitrile so as to detoxify the herbicidal activity of the nitrile and provide protection to a cell or host sensitive to the herbicide or detoxify an environment contaminated with the herbicide.

The structural gene of interest may be obtained from a unicellular microorganism, particularly a bacterium, which is shown to be capable of employing the benzonitrile as a nitrogen source, usually being capable of employing the benzonitrile as the exclusive nitrogen source. Hereafter, in referring to benzonitrile or a nitrilase, it is intended that the benzonitrile be a halogenated p-hydroxybenzonitrile, particularly 3,5-diiodo-or 3,5-dibromo-4-hydroxybenzonitrile, and the nitrilase is a nitrilase which is capable of using such halogenated benzonitrile as a nitrogen source, particularly as its exclusive nitrogen source.

The enzyme can be obtained in different ways, conveniently from bacteria which exist naturally in an environment containing bromoxynil or ioxynil. Particularly, enteric bacteria, more particularly of the species Klebsiella, are of interest. *Klebsiella pneumoniae* may be employed, more particularly var. oazenae. Rather than isolation from soil, organisms may be grown in soil or other medium at increasingly higher concentrations of the benzonitrile and reduced amounts of alternative nitrogen sources until organisms which survive employing the benzonitrile as the sole nitrogen source are obtained.

Regardless of the source of the bacterium containing the nitrilase, screening must be performed to insure that the nitrilase is efficient in the detoxification of the benzonitrile. In addition, the nitrilase should be specific for the benzonitrile rather than other analogs, which lack the halogens, have other substituents, or the like. The nitrilase of this invention will therefore be specific for the benzonitriles, as defined, and be relatively inactive toward analogs or substantially less active toward analogs. Desirably, there should be no significant reduction in rate of proliferation, that is, less than about 10% reduction, of the proliferation of the bacterium in the presence of a normal nitrogen source, e.g. ammonia, as compared to the benzonitrile as the nitrogen source at comparable concentrations. Such result will not be observed with non-specified benzonitriles.

Once one or more host strains have been identified, techniques may then be employed to identify the coding sequence for the nitrilase. The gene may be present on a chromosome or plasmid. The genome may be fragmented, particularly with a restriction endonuclease, where one or a multiple of endonucleases may be employed to provide fragments ranging from about 5kb to 50kb. These fragments may be cloned on appropriate vectors in a convenient bacterium, e.g., *E. coli*, and the resulting transformants screened for nitrilase activity, where the host organism provides a negative background.

Once one or more clones have been identified as having nitrilase activity, the extrachromosomal elements containing the desired DNA fragment, plasmids or viruses, may be isolated by conventional techniques, such as lysis of the host, precipitation of the DNA, and separation of the vector DNA, plasmid or virus DNA, from the chromosomal DNA. The extrachromosomal elements may then be cleaved by endonuclease restriction and the desired fragments isolated by various techniques for separation and identification of different sized fragments, e.g., electrophoresis, density gradient centrifugation, or the like.

Depending upon the size of the fragment, it will usually be further manipulated to reduce the size to more closely approximate the size of the gene and its flanking regulatory regions. Various techniques exist for manipulating the fragment containing the sequence coding for the enzyme and its regulatory flanking sequences. Partial cleavage with different restriction enzymes in different reaction mixtures may be employed, followed by cloning of the fragments to determine which fragments still retain the ability to provide expression of the nitrilase.

Alternatively, the enzyme may be isolated and partially sequenced. Based on the amino acid sequence, probes can be prepared which may then be used to identify those fragments having the gene. By combining this approach with restriction enzyme cleavage, fragments can be cloned and screened for the presence of the desired gene. In addition, one may use exonucleases, such as Bal31 to remove nucleotides from one or both ends of the fragment to further reduce the number of superfluous nucleotides.

Alternatively, the gene may be cloned in an appropriate host and messenger RNA isolated by screening with a probe, by identification in an appropriate in vitro or in vivo translation system, e.g., Xenopus oocytes or reticulolysate, or the like. The isolated messenger may then be used for preparing cDNA using conventional techniques involving a reverse transcriptase and formation of the complementary chain with a DNA polymerase. In this instance, the resulting structural gene lacks the regulatory regions associated with transcription.

The nitrilase gene may be modified in a variety of ways, truncating either or both the 5'- or 3'-termini, extending the 5'- or 3'-termini. Usually, not more than 25, more usually not more than about 20 condons will be involved of the naturally occurring nitrilase. The nitrilase may be extended by as many as 50 amino acids, usually not more than about 30 amino acids. Combinations of substitution, truncation and extension may be employed. Thus, the gene may be manipulated in a variety of ways to change the characteristics of the enzyme, for convenience in manipulation of the plasmids, or the like.

The DNA sequence containing the structural gene expressing the nitrilase may be joined to a wide variety of other DNA sequences for introduction into an appropriate host cell. The companion sequence will depend upon the nature of the host, the manner of introduction of the DNA sequence into the host, and whether episomal maintenance or integration is desired.

For prokaryotic hosts, a wide variety of vectors exist which may be used for introduction by transformation, conjugation, transduction or transfection of the DNA sequence into a prokaryotic host. DNA sequences include a wide variety of plasmids, such as pBR322, pA-CYC184, pMB9, pRK290, etc.; cosmids, such as pVK100; or virus, such as P22, etc.

For eukaryotic hosts, a wide variety of techniques may be employed for DNA introduction into the host, such as transformation with $Ca^{++}$—precipitated DNA, involving a non-replicating DNA sequence, a plasmid or a minichromosome, transformation with a T-DNA containing sequence in Agrobacterium, microinjection with a micropipette, or electroporation. Depending upon whether a competent replication system is present in the DNA construction, will determine whether the DNA may be replicated as an episomal element, or the DNA may be integrated into the host genome, and the structural gene expressed in the host. Episomal elements may be employed, such as tumor inducing plasmids, e.g., Ti or Ri, or fragments thereof, or viruses, e.g., CaMV, TMV or fragments thereof, which are not lethal to the host, and where the structural gene is present in such episomal elements in a manner allowing for expression of the structural gene. Particularly of interest are fragments having the replication function and lacking other functions such as oncogenesis, virulence, etc.

The fragments obtained from the nitrilase source may be cloned employing an appropriate cloning vector. Cloning can be carried out in an appropriate unicellular microorganism, e.g., a bacterium, such as *E. coli*. Desirably, one may use a cosmid, where partial or complete digestion provides fragments having about the desired size. For example, the cosmid pVK100 may be partially digested with an appropriate restriction enzyme and ligated to fragments resulting from either partial or complete digestion of a plasmid, chromosome, or fragment thereof. Packaging will insure that only fragments of the desired size will be packaged and transduced into the host organism.

The host organism may be selected for benzonitrile resistance. The recipient strains may be modified to provide for appropriate genetic traits which allow for selection of transductants. In microorganisms, the transductants may be used for conjugation to other microorganisms, using a mobilizing plasmid as required. Various techniques may be used for further reducing the size of the fragment containing the structural gene for the nitrilase. For example, the cosmid vector may be isolated, cleaved with a variety of restriction endonucleases, e.g., EcoRI, BglII, SmaI, etc., and the resulting fragments cloned in an appropriate vector, conveniently the cosmid vector previously used. Instead of a cosmid vector, a variety of cloning vectors are available of small size, such as pACYC177 and pACYC184. Thus, fragments of preferably less than about 5kb, usually less than about 4kb, and more preferably less than about 2kb, can be cloned and provide for benzonitrile resistance.

Desirably, the fragment will be about 1kb and less than about 5kb, preferably less than about 4kb, particularly at least about 1047bp, more particularly including flanking regions of at least about 1100bp, preferably less than about 1.5kb. Of particular interest, is a BglII-SmaI fragment from *Klebsiella ozaenae*, more particularly a PstI-HincII fragment of about 1210bp.

Of particular interest is truncaction of the nitrilase gene by up to about 5 codons at the 5'-terminus and up to about 10 codons at the 3'-terminus, or up to about 50, usually not more than about 30, preferably not more than 20 codons are added at the 5'- and/or 3'-terminus. Thus, the resulting enzyme may differ from the naturally occuring enzyme by as many as 50 amino acids, more usually not more than about 30 amino acids, preferably by not more than about 25 amino acids, involving a combination of substitution, extension and truncation.

The nitrilase enzyme may be expressed by any convenient source, either prokaryotic or eukaryotic, including bacteria, yeast, filamentous fungus, plant cells, etc. Where secretion is not obtained, the enzyme may be isolated by lysing the cells and isolating the nitrilase according to known ways. Useful ways include chromatography, electrophoresis, affinity chromatography, and the like. Conveniently, bromoxynil may be conjugated through an appropriate functionality, e.g., the carboxyl group, to an insoluble support and used as a packing for the isolation of the nitrilase.

The nitrilase specific activity will be at least about 0.1 umol ammonia/min/mg protein, generally at least about 0.5 or higher under conditions as described by Harper, *Biochem. J.* (1977) 167:685–692.

The purified enzyme can be used in a wide variety of ways. It may be used directly in assays for bromoxynil, ioxynil, or other related benzonitriles. Alternatively, the subject enzyme can find use as a label in diagnostic assays, by being conjugated to an analyte of interest, e.g., a hapten or antigen, or to an antibody, as such assays are described in U.S. Pat. Nos. 3,654,090; 3,817,837; and 3,850,752. The methods of conjugation, as well as the determination of the concentration of an analyte are described in extensive detail in these patents, and the appropriate portions of their disclosures are incorporated herein by reference.

The DNA sequence encoding for the nitrilase may be used in a variety of ways. The DNA sequence may be used as a probe for isolation of wild type or mutated nitrilases. Alternatively, the DNA sequence may be used for integration by recombination into a host to provide for imparting benzonitrile resistance to the host.

With plant cells, the structural gene as part of a construction may be introduced into a plant cell nucleus by micropipette injection for integration by recombination into the host genome. Alternatively, electroporation may be employed for introduction of the structural gene into a plant host cell. Where the structural gene has been obtained from a source having regulatory signals which are not recognized by the plant host, it may be necessary to introduce the appropriate regulatory signals for expression. Where a virus or plasmid, e.g. tumor inducing plasmid, is employed and has been mapped, a restriction site can be chosen which is downstream from a promoter into which the structural gene may be inserted at the appropriate distance from the promoter. Where the DNA sequences do not provide an appropriate restriction site, one can digest for various times with an exonuclease, such as Bal31 and insert a synthetic restriction endonuclease site (linker).

Of particular interest is the use of a tumore-inducing plasmid, e.g., Ti or Ri, where the nitrilase gene may be integrated into plant cell chromosomes. Descriptions of the use of Ti-plasmids and Ri-plasmids may be found in PCT Publication Nos. WO84/02913, 02919 and 02920 and EPO Application 0 116 718, and Matzke and Chilton, *J. Mol. App. Genetics* (1981) 1:39–49.

By employing the T-DNA right border, or both borders, where the borders flank an expression cassette comprising the nitrilase structural gene under transcriptional and translational regulatory signals for initiation and termination recognized by the plant host, the expression cassette may be integrated into the plant genome and provide for expression of the nitrilase enzyme in the plant cell at various stages of differentiation.

Various constructs can be prepared providing for expression in plant cells. The constructs provide an expression cassette which is functional in plants for expression of the nitrilase in the plant host.

To provide for transcription, a variety of transcriptional initiation regions (promoter regions), either constitutive or inducible, may be employed.

The transcriptional initiation region is joined to the structural gene encoding the nitrilase to provide for transcriptional initiation upstream from the initiation codon, normally within about 200 bases of the initiation codon, where the untranslated 5'-region lacks an ATG.

The 3'-end of the structural gene will have one or more stop codons which will be joined to a transcriptional termination region functional in a plant host, which termination region may be associated with the same or different structural gene as the initiation region.

The expression cassette is characterized by having in the direction of transcription the initiation region, the structural gene under the transcriptional control of the initiation region, and the termination region providing for termination of transcription and processing of the messenger RNA, as appropriate.

As transcriptional and translational regulatory regions, conveniently opine promoter and terminator regions may be employed, which allow for constitutive expression of the nitrilase gene. Alternatively, other promoters and/or terminators may be employed, particularly promoters which provide for inducible expression ore regulated expression in a plant host. Promoter regions which may be used from the Ti-plasmid include opine promoters, such as the octopine synthase promoter, nopaline synthase promoter, agropine sunthase promoter, mannopine synthase promoter, or the like. Other promoters include viral promoters, such as CaMV Region VI promoter or full length (35S) promoter, the promoters associated with the ribulose-1,5-bisphosphate carboxylate genes, e.g., the small subunit, genes associated with phaseolin, protein storage, B-conglycinin, cellulose formation, or the like.

The various sequences may be joined together in conventional ways. The promoter region may be identified by the region being 5' from the structural gene, for example, the opine gene, and by restriction mapping and sequencing may be selected and isolated. Similarly, the terminator region may be isolated as the region 3' from the structural gene. The sequences may be cloned and joined in the proper orientation to provide for constitutive expression of the nitrilase gene in a plant host.

By modifying crop plant cells by introduction of a functional gene expressing the nitrilase enzyme, one can use bromoxynil, ioxynil, or analogous herbicide with a wide variety of crops at concentrations which ensure the substantially complete or complete removal of weeds, while leaving the crop relatively unaffected. In this manner, substantial economies can be achieved in that fertilizers and water may be more efficiently utilized, and the detrimental effects resulting from the presence of weeds avoided.

The expression cassette expressing the nitrilase enzyme may be introduced into a wide variety of plants, both monocotyledon and dicotyledon, including maize, wheat, soybean, tobacco, cotton, tomatoes, potatoes, Brassica species, rice, peanuts, petunia, sunflower, sugar beet, turfgrass, etc. The gene may be present in cells or plant parts including callus, tissue, roots, tubers, propagules, plantlets, seed, leaves, seedlings, pollen, or the like.

By providing for benzonitrile-resistant plants, a wide variety of formulations may be employed for protecting crops from weeds, so as to enhance crop growth and reduce competition for nutrients. For example, bromoxynil could be used by itself for postemergence control of weeds with safened crops, such as sunflower, soybeans, corn, cotton, etc., or alternatively, in combination formulations with other products.

Conventional amounts of the pesticides would be applied to fields in the formulations to deliver from about 0.1 to 4 lb/acre, preferably 0.2 to 2 lb/acre, of bromoxynil, where the other herbicide would be in amounts to deliver from about 0.1 to 4 lb/acre of active ingredient. Formulations would include other additives, such as detergents, adjuvants, spreading agents, sticking agents, stabilizing agents, or the like. The formulations may either be wet or dry formulations, including flowable powders, emulsifiable concentrates and liquid concentrates, as in known in the art.

The herbicidal solutions may be applied in accordance with conventional ways, for example, through spraying, irrigation, dusting, or the like.

The following examples are offered by way of illustration and not by way of limitation.

EXPERIMENTAL

Materials and Methods

Restriction enzymes and T4 ligase for ligations were utilized according to the manufacturer's recommendations. Standard methods in cloning and molecular analysis were performed according to Maniatis et al., (1982) *Molecular Cloning: A Laboratory Manual*, Cold Spring Harbor Laboratory, New York. Clone analysis was performed as described by Ish-Horowitz et al., *Nucl. Acids Res.* (1981) 9:2989–2998.

*E. coli* strain MM294 was used for all cloning experiments. (Hanahan, *Mol. Biol.* (1983) 166:557–80.)

The levels of antibiotics when employed were: Cm (chloramphenicol) 25 ug/ml; Tc (tetracycline) 10 ug/ml; Ap (penicillin) 300 ug/ml.

Transformations of plasmid DNAs in *E. coli* were performed according to Mandel and Higa, *J. Mol. Biol.* (1970) 53:159–162.

Bacterial isolates from a bromoxynil contaminated soil sample were isolated and screened. One such organism was identified as *Klebsiella pneumoniae* sub-species ozaenae. Partial purification and characterization of the bromoxynil specific and nitrilase from the above organism yielded an active enzyme with an apparent molecular weight of 34kDal.

Upon repeated subculturing of *K. ozaenae* on solid L-agar, a variant was isolated which no longer was able to utilize bromoxynil as a sole nitrogen source when this variant organism was grown in defined liquid medium containing per liter $KH_2PO_4$ (1.5 g), $K_2HPO_4$ (3.5 g), $MgSO_4.7H_2O$ (0.1 g), yeast extract (50 mg), citrate, glycerol and succinate at 0.1%, and trace elements as described by Barnett and Ingraham, *J. Appl. Bacteriol.* (1975) 18:131–143. This medium henceforth will be known as YETE multi-carbon medium. The YETE multicarbon medium contained 0.05% bromoxynil. Although this organism did not utilize bromoxynil as sole nitrogen source, it would grow to full density in L-broth containing 0.05% bromoxynil. A *K. oxaenae* variant colony was selected and grown in 10 mls of L-broth. Three independent *K. ozaenae* colonies were also chosen from a LB plate containing bromoxynil and grown under the same conditions. These same four *K. ozaenae* colonies were simultaneously grown in 10 mls L-broth supplemented with 0.05% bromoxynil. Cultures were grown to full density to 30° C. and mini-prep plasmid DNA prepared from each culture by the method of Ish-Horowitz et al., *Nucl. Acids Res.* (1981) 9:2989. Undigested plasmid DNAs were electrophoresed on a 0.5% agarose gel and the plasmid bands visualized by ethidium bromide straining.

The *K. ozaenae* variant organism revealed a single plasmid species (68Kb in size) grown either in the presence or absence of bromoxynil. The three *K. ozaenae* colonies showed a larger plasmid species (90Kb) when grown in the presence of 0.05% bromoxynil. In the absence of bromoxynil, both plasmid forms are present in two of the three *K. oxaenae* colonies. This data indicates conversion of the larger plasmid species to a smaller form with the concommitant loss of approximately 22Kb of plasmid DNA when bromoxynil selection is relieved.

All four colonies were grown in 200 mls L-broth containing 0.05% bromoxynil. Cells were disrupted with a French press, the high speed supernatants dialyzed against buffer containing 0.05M KPO, pH7.5; 2.5 mM dithiothreitol (DTT) and the individual crude extracts assayed for bromoxynil specific nitrilase activity. A crude extract prepared from the *K. ozaenae* variant contained no detectable nitrilase activity while the other *K. ozaenae* crude extracts exhibited nitrilase specific activities of 0.124, 0.105 and 0.143 umole $NH,/min/mg$ protein respectively. Cells (200 ml) were grown at 30° C. to mid log phase in M9 medium (Miller (1972) Experiments in Molecular Genetics, Cold Spring Harbor Laboratory) containing 0.1% glucose and 0.04% bromoxynil. Crude extracts were prepared by cell disruption, ultracentrifugation and dialysis of the supernatant in buffer containing 0.05M $KPO_4$ pH 7.5 and 2.5 mM DTT. Substrate concentarion was 3 mM bromoxynil in all assays. Release of $NH_3$ was monitored according to Harper *Biochem. J.* (1977) 167:685–692. The ability of *K. ozaenae* variant to grow in L-broth containing bromoxynil may result in acquired impermeability of the organism to the compound. However, the organism cannot grow in defined media utilizing bromoxynil as sole nitrogen source.

In summary, the *K. ozaenae* nitrilase appears to be plasmid encoded. The gene(s) encoding the enzyme appears to reside on a 22Kb plasmid DNA segment spontaneously lost from the *K. ozaenae* plasmid in the absence of bromoxynil selection. The *K. ozaenae* bromoxynil specific nitrilase is expressed in *E. coli.*

Plasmid DNA from *K. ozaenae* grown under 0.05% bromoxynil selection was prepared and the DNA transformed to *E. coli* strain MM294 (thi, gyrA96, endI$^-$, hsdR17). Transformants were selected on nitrogen deficient (N$^-$) solid agarose minimal medium (containing per liter $KH_2PO_4$ (1.5 g), $K_2HPO_4$ (3.5 g), $MgSO_4.7H_2O$ (0.1 g) and 0.1% glucose) with the addition of 0.05% bromoxynil as sole nitrogen source. After 5 days incubation, 10 colonies appeared on the selective plates. These colonies were restreaked on L-agar plates containing 0.05% bromoxynil and tested for the presence of the thiamine auxotrophic marker in MM294. None of the colonies grew in minimal media in the absence of thiamine indicating the strain to be *E. coli* MM294. All colonies could grow in M9 medium supplemented with thiamine and 0.05% bromoxynil as sole nitrogen source.

No growth was observed in this medium in the absence of bromoxynil. Two of the colonies were selected for further analysis. When crude extract preparations of E. coli MM294 containing the 90kb plasmid were assayed for bromoxynil specific nitrilase activity, a specific activity of 0.216 umole NH₃ released/min/mg was obtained. E. coli MM294 containing the smaller plasmid species produced no detectable nitrilase activity. The larger 90Kb plasmid in E. coli was designated pBrx1 while the smaller plasmid (68Kb) was designated pBrx1Δ.

To confirm that E. coli strain MM294 containing plasmid pBrx1 produces the proper metabolite as a result of a bromoxynil specific nitrilase reaction, a 2 ml culture of MM294 (pBrx1) was grown for 24 hr at 30° C. in M9 medium supplemented with 0.05% bromoxynil. A culture filtrate sample was chromatographed on a $C_{18}$HPLC column. All input bromoxynil in the culture filtrate was converted to a new metabolite peak. The identity of the metabolite peak was determined by spectral analysis to be 3'5'-dibromo-4-hydroxybenzoic acid (DBHB). Thus, the product of the bromoxynil specific plasmid encoded nitrilase expression in E. coli is the same as that observed for K. ozaenae.

The bromoxynil specific nitrilase gene is cloned in E. coli.

To determine whether the DNA segment encoding the bromoxynil specific enzyme is clonable in E. coli, plasmid pBrx1 was digested with BamHI resulting in two bands of 53Kb and 37Kb, respectively. The BamHI fragments were ligated into the BamHI site of the E. coli plasmid vector pACYC184 (Chang and Cohen, J. Bacteriol. (1978) 134:1141) and transformed to E. coli strain MM294. Cloning into the BamHI site of pACYC184 results in insertional inactivation of the tetracycline resistance gene. Ten chloramphenicol resistant tetracycline sensitive MM294 colonies were selected, miniprep clone analysis DNA prepared and the DNA digested with BamHI. Four clones contained the 37Kb BamHI fragment while one clone harbored the larger 53Kb BamHI DNA fragment of pBrx1. Five clones contained a cloned BamHI fragment also found in plasmid pBrx1Δ which corresponds to the DNA segment remaining after spontaneous deletion of 22Kb of plasmid DNA from pBrx1. All 10 clones were grown in 200 ml L-broth in the presence of 20 ug/ml chloramphenical (to select for the plasmid), crude extract preparations obtained and assayed for bromoxynil specific nitrilase activity. Four clones containing the 37Kb BamHI fragment exhibited nitrilase specific activities in the range of 0.140 umole NH₃ released/min/mg protein while no detectable nitrilase activity was observed in the other six clones. This data indicates the gene encoding a bromoxynil specific nitrilase activity is located on a 37Kb BamHI fragment cloned from plasmid pBrx1 and that the 22Kb DNA segment spontaneously lost in the absence of bromoxynil selection is internal to the 37Kb BamHI fragment.

To confirm the orientation of the BamHI fragments with respect to the vector pACYC184, DNA from the above four clones was digested with EcoRI and electrophoresed on a 0.07% agarose gel. A combined EcoRI digest of plasmids pBrx1 and pBrx1Δ was also analyzed.

Both orientations of the 37Kb BamH7 fragment with respect to the vector pACYC184 were defined and designated plasmids pBrx2 and pBrx3, respectively. It was also observed that the three EcoRI fragments are internal to the 22Kb DNA segment that is spontaneously deleted from plasmids pBrx2 and pBrx3. The sizes of these EcoRI fragments are 18Kb, 3Kb and 1.9Kb, respectively. The gene encoding the bromoxynil specific nitrilase should be located within one of these three EcoRI fragments if the nitrilase structural gene is not bisected by an EcoRI restriction site.

Localization of the bromoxynil specific nitrilase of E. coli (pBrx3) was investigated. The results were as follows.

TABLE 1

The Bromoxynil Specific Nitrilase is a Periplasmic Enzyme in E. coli.

| Culture Conditions[a] | Nitrilase Specific Activity[b] |
|---|---|
| toluenized cells (L-broth) | 0.829 |
| lysozyme treated cells (L-broth) | 0.796 |
| whole cells (L-broth) | 0.770 |
| whole cells (L-broth + Brxl) | 1.25 |
| whole cells (M9) | 0.950 |
| whole cells (M9 + Brxl) | 1.45 |
| whole cells/pACYC184 (M9) | 0 |

[a]E. coli (MM294) cells containing plasmid pBrx3 were grown to stationary phase in 5 ml cultures at 37° in medium indicated. Cultures contained 20 ug/ml chloramphenicol and 0.04% bromoxynil (Brxl) where indicated. One ml from each culture was harvested, washed once with nitrilase buffer (0.1 M KPO₄ pH 7.5) and cells resuspended in 0.1 ml of this same buffer. 50 ul samples were assayed for nitrilase activity according to Harper, Biochem. J. (1977) 167:685–692, with and without 3 mM bromoxynil as substrate.
[b]umole NH₃/min/mg. Protein was determined as O.D.₆₀₀ of 1.4 = 10⁹ cells/ml = 150 ug.

These data indicate the the cellular location of the nitrilase enzyme is the periplasmic space. A second observation is that the enzyme is expressed in the absence of bromoxynil in the medium suggesting that bromoxynil induction is not required for enzyme expression.

Further purification of the bromoxynil specific nitrilase.

Further purification of K. ozaenae nitrilase was carried out with the following results.

TABLE 2

Purification from E. coli of the Bromoxynil Specific Nitrilase. (Starting material 6 gms cells)

| Fraction | Volume | Protein | umole NH₃/min | S.A.[b] |
|---|---|---|---|---|
| Crude[a] | 100 ml | 210 mg | 18.15 | 0.086 |
| 35–50% NH₄SO₄ | 6 ml | 83 mg | 26.77 | 0.250 |
| DEAE Sephadex | 56 ml | 19 mg | 15.52 | 0.820 |

[a]Cells were grown at 30° to mid log phase in M9 medium containing 0.04% bromoxynil and glucose. Crude extracts were prepared by cell disruption, ultracentrifugation and dialysis in buffer containing 0.05 M KPO₄ pH 7.5 and 2.5 mM DTT. Substrate concentration was 3 mM in all nitrilase assays.
[b]umole NH₃/min/ng A 2.5 cm²×10 cm column was equilibrated in buffer containing 0.05% KPO₄ pH7.5, 2.5 mM DTT and 1 mM EDTA. The sample was applied and the column developed with a 300 ml linear gradient of 0.02M to 0.40M NaCl in the above column buffer. Buffer containing 1M NaCl was applied at the end of the gradient. 5 ml fractins were collected and 0.075 ml aliquots of alternate fractions assayed for nitrilase activity. A single peak of enzyme activity eluted at 0.22M salt. Approximately 75% of the input nitrilase activity was recovered in the active fractions.

Fractions spanning the nitrilase peak from the DEAE column were dialyzed against 0.02M KPO₄ pH 7.5 and 50 ul (6 ug protein) of each fraction applied to an 11.25% denaturing Laemmli gel. The enriched protein band that corresponds to the activity peak from the DEAE column is a polypeptide of 34,000 molecular weight. No other polypeptides were enriched by the active column fractions. These data support that the bromoxynil specific nitrilase is a polypeptide of approximately 34,000 molecular weight and probably the product of a single gene.

Clone pBrx2 was completely digested with EcoRI and an approximately 19kb fragment isolated. The fragment was inserted into the EcoRI-digested pACYC184 vector (3.9kb) to provide the plasmid pBrx5 which was transformed into *E. coli* as described previously. The plasmid was isolated in conventional ways and digested with BglII to provide an approximately 6.7kb fragment which remained inserted in the pACYC184 vector. The isolated plasmid pBrx7 was then digested with SmaI and BglII to provide an approximately 3.9kb fragment which was inserted into SmaI-BamHI digested pACYC177 (3.7kb) (Chang and Cohen, *J. Bacteriol.* (1978) 134:1141-1156). The resulting plasmid which provided penicillin resistance was transformed into *E. coli* as described previously and transformants selected on penicillin selected medium to provide plasmid pBrx8, which carries the nitrilase gene on a 3.9kb fragment.

pBrx8 is partially digested with PstI and the fragments inserted into PstI digested pUC18 (Yanisch-Perron et al., *Gene* (1985) 33:103-119). The resulting plasmids were cloned in *E. coli* and screened for nitrilase activity. One clone had a 5.3kb plasmid pBrx9 which was isolated and further digested with PstI and HincII resulting in a 1210bp fragment having in the direction of PstI to HincII, ClaI, SalI, ScaI, and SphI restriction sites relatively evenly spaced. The PstI-HincII fragment was sequenced according to the method of Sanger et al., *Proc. Natl. Acad. Sci. U.S.A.* (1977) 74:5463-5468. The resulting sequence (with the appropriate amino acids encoded) is set forth in the following sequence.

CTGCAGGATAGTAGGGGCTTGAAGAGGATACGCTGTTTGGCGAGCCATCAAAATAAGGGGATTTTC 65

| | | | | | | | | | | | | | | | | | | | |
|---|---|---|---|---|---|---|---|---|---|---|---|---|---|---|---|---|---|---|---|
| ATG | GAC | ACC | ACT | TTC | AAA | GCA | GCC | GCT | 95 GTT | CAG | GCC | GAA | CCG | GTA | TGG | ATG | GAT | GCC | 125 GCT |
| Met | Asp | Thr | Thr | Phe | Lys | Ala | Ala | Ala | Val | Gln | Ala | Glu | Pro | Val | Trp | Met | Asp | Ala | Ala |
| GCA | ACA | GCC | GAT | AAG | ACC | GTG | ACG | CTA | 155 GTA | GCT | AAA | GCC | GCA | GCG | GCT | GGC | GCG | CAG | 185 CTC |
| Ala | Thr | Ala | Asp | Lys | Thr | Val | Thr | Leu | Val | Ala | Lys | Ala | Ala | Ala | Ala | Gly | Ala | Gln | Leu |
| GTC | GCA | TTT | CCC | GAA | TTG | TGG | ATT | CCG | 215 GGC | TAC | CCA | GGA | TTC | ATG | CTC | ACG | CAC | AAC | 245 CAA |
| Val | Ala | Phe | Pro | Glu | Leu | Trp | Ile | Pro | Gly | Try | Pro | Gly | Phe | Met | Leu | Thr | His | Asn | Gln |
| ACC | GAA | ACC | CTA | CCA | TTC | ATC | ATT | AAA | 275 TAC | CGC | AAG | CAG | GCA | ATC | GCC | GCC | GAT | GGA | 305 CCA |
| Thr | Glu | Thr | Leu | Pro | Phe | Ile | Ile | Lys | Try | Arg | Lys | Gln | Ala | Ile | Ala | Ala | Asp | Gly | Pro |
| GAA | ATC | GAA | AAA | ATT | CGC | TGC | GCG | GCT | 335 CAG | GAG | CAT | AAC | ATT | GCG | CTC | TCC | TTT | GGG | 365 TAC |
| Glu | Ile | Gu | Lys | Ile | Arg | Cys | Ala | Ala | Gln | Glu | His | Asn | Ile | Ala | Leu | Ser | Phe | Gly | Tyr |
| AGC | GAA | CGG | GCT | GGC | CGT | ACT | CTC | TAC | 395 ATG | TCA | CAA | ATG | CTT | ATC | GAT | GCC | GAT | GGC | 425 ATC |
| Ser | Glu | Arg | Ala | Gly | Arg | Thr | Leu | Tyr | Met | Ser | Gln | Met | Leu | Ile | Asp | Ala | Asp | Gly | Ile |
| ACC | AAA | ATT | CGT | CGT | CGA | AAG | CTC | AAA | 455 CCA | ACC | CGC | TTT | GAA | CGA | GAA | CTC | TTT | GGC | 485 GAA |
| Thr | Lys | Ile | Arg | Arg | Arg | Lys | Leu | Lys | Pro | Thr | Arg | Phe | Glu | Arg | Glu | Leu | Phe | Gly | Glu |
| GGT | GAC | GGA | TCG | GAC | TTA | CAG | GTC | GCC | 515 CAA | ACT | AGC | GTT | GGT | CGG | GTG | GGT | GCC | CTC | 545 AAC |
| Gly | Asp | Gly | Ser | Asp | Leu | Gln | Val | Ala | Gln | Thr | Ser | Val | Gly | Arg | Val | Gly | Ala | Leu | Asn |
| TGC | GCG | GAG | AAT | TTG | CAG | TCG | CTA | AAC | 575 AAC | TTT | GCG | CTT | GCT | GCC | GAG | GGT | GAA | CAG | 605 ATA |
| Cys | Ala | Glu | Asn | Leu | Gln | Ser | Leu | Asn | Lys | Phe | Ala | Leu | Ala | Ala | Glu | Gly | Glu | Gln | Ile |
| CAT | ATC | TCC | GCC | TGG | CCA | TTC | ACG | CTT | 635 GGA | AGC | CCT | GTG | CTC | GTC | GGA | GAC | TCC | ATC | 665 GGC |
| His | Ile | Ser | Ala | Trp | Pro | Phe | Thr | Leu | Gly | Ser | Pro | Val | Leu | Val | Gly | Asp | Ser | Ile | Gly |
| GCC | ATC | AAC | CAG | GTC | TAC | GCG | GCC | GAG | 695 ACG | GGG | ACC | TTC | GTT | CTC | ATG | TCG | ACG | CAG | 725 GTG |
| Ala | Ile | Asn | Gln | Val | Tyr | Ala | Ala | Glu | Thr | Gly | Thr | Phe | Val | Leu | Met | Ser | Thr | Gln | Val |
| GTT | GGA | CCG | ACC | GGC | ATC | GCC | GCC | TTC | 755 GAG | ATC | GAA | GAC | AGG | TAC | AAC | CCG | AAT | CAG | 785 TAT |
| Val | Gly | Pro | Thr | Gly | Ile | Ala | Ala | Phe | Glu | Ile | Glu | Asp | Arg | Tyr | Asn | Pro | Asn | Gln | Tyr |
| CTT | GGT | GGT | GGG | TAC | GCG | CGG | ATC | TAC | 815 GGG | CCT | GAC | ATG | CAG | TTG | AAG | AGC | AAG | TCG | 845 TTG |
| Leu | Gly | Gly | Gly | Tyr | Ala | Arg | Ile | Tyr | Gly | Pro | Asp | Met | Gln | Leu | Lys | Ser | Lys | Ser | Leu |

-continued

| TCA Ser | CCG Pro | ACC Thr | GAA Glu | GAG Glu | GGC Gly | ATC Ile | GTC Val | TAC Tyr | 875 GCC Ala | GAG Glu | ATC Ile | GAC Asp | CTG Leu | TCG Ser | ATG Met | CTT Leu | GAG Glu | GCA Ala | 905 GCA Ala |
| AAG Lys | TAC Tyr | TCG Ser | CTC Leu | GAT Asp | CCC Pro | ACG Thr | GGC Gly | CAC His | 935 TAT Tyr | TCG Ser | CGC Arg | CCT Pro | GAT Asp | GTG Val | TTC Phe | AGC Ser | GTG Val | TCG Ser | 965 ATT Ile |
| AAC Asn | CGG Arg | CAA Gln | CGG Arg | CAG Gln | CCT Pro | GCG Ala | GTG Val | TCA Ser | 995 GAA Glu | GTT Val | ATC Ile | GAC Asp | TCA Ser | AAC Asn | GGT Gly | GAC Asp | GAG Glu | GAC Asp | 1025 CCG Pro |
| AGA Arg | GCA Ala | TGC Cys | GAG Glu | GAG Glu | CCC Pro | GAC Asp | GAG Glu | GGG Gly | 1055 GAT Asp | CGT Arg | GAG Glu | GTC Val | GTA Val | ATC Ile | TCT Ser | ACG Thr | GCA Ala | ATA Ile | 1085 GGG Gly |
| GTT Val | CTA Leu | CCC Pro | CGT Arg | TAT Tyr | TGC Cys | GGA Gly | CAT His | TCC Ser | 1115 TAATAAAAGAGACACGTGGTACCAAAGGGGTGTTCATGTCCA 1155 |

1200 GACGCAGAAAATAGCCCAGAGTTAAAACGCGAAGCCATCGCTTTAACCCGTCAAC

The PstI-HincII fragment substantially free of 5'- and 3'-non-coding flanking regions may be ligated with EcoRI linkers, digested with EcoRI and is now ready to be introduced into a plant expression cassette by insertion into the EcoRI site of pCGN451.

pCGN451 includes an octopine cassette which contains about 1,566bp of the 5' non-coding region fused via an EcoRI linker to the 3' end of the gene and about 1,349bp of 3' non-coding DNA. The pTi coordinates are 11,207 to 12,823 for the 3' region and 13,643 to 15,208 for the 5' region as defined by Barker et al., *Plant Molecular Biology* (1983) 2:335. The 5' fragment was obtained as follows: A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case the entire coding region and 10bp of the 5' non-translated sequences had been removed leaving the 5' non-transcribed region, the mRNA cap site and 16bp of the 5' non-translated region (to a BamHI site) intact. This small fragment was obtained by size fractionation on a 7% acrylamide gel and fragments approximately 130bp long eluted. This size fractionated DNA was ligated into M13mp9 and several clones sequenced and the sequence compared to the known sequence of the octopine synthase gene. The M13 construct was designated pI4, which plasmid was digested with BamHI and EcoRI to provide the small fragment which was ligated to an XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550bp of 5' non-transcribed sequence including the right border of the T-DNA, the mRNA cap site and 16bp of 5' non-translated sequence) and the 3' region (which contains 267 bp of the coding region, the stop codon, 196bp of 3' non-translated DNA, the polyA site and 1,153bp of 3' non-transcribed sequence).

The XhoI fragment containing the octopine synthase (ocs) cassette was inserted into plasmid pCGN517, which has tetracycline resistance and kanamycin resistance genes. pCGN517 was prepared from pHC79 (Hohn, *Gene* (1980) 11:291) by introducing into the unique PstI site, the Kan gene from pUC4K (Vieira, *Gene* (1982) 19:259). pCGN517 was digested with SalI and the XhoI fragment inserted into the unique SalI site.

The XhoI fragment was also inserted into a second plasmid pCGN529. pCGN429 is prepared from pACYC184 by insertion of the Kan gene from Tn5 (Rothstein et al., 1981, in *Movable Genetic Elements*, p. 99, Cold Spring Harbor Laboratories, Cold Spring Harbor, N.Y.) and a BglII fragment of 2.4kb from pRiA4 T-LDNA (White and Nester, *J. Bacteriol.* (1980) 144:710) inserted into the BamHI site remaining after substitution of the HindIII-BamHI fragment of pACYC184 with the Kan gene of Tn5.

The XhoI fragment containing the ocs cassette into which the EcoRI nitrilase gene is inserted at the unique EcoRI of the ocs cassette is inserted into pCGN517 and pCGN529 to give two plasmids pN1 and pN2, respectively, which are used for introduction into *A. tumefaciens* or *A. rhizogenes*, respectively, for integration to the T-DNA of the Ti- or Ri-plasmids. Integration into the respective plasmids can be achieved in a 3-way mating as described by Comai et al., *Plasmid* (1983) 10:21–30. Overnight cultures of *E. coli* host containing plasmids pRK2073, pN1 or pN2 and *A. tumefaciens* A722 (Garfinkel, *J. Bacteriol.* (1980) 144:732) or *A. rhizogenes* A4T (White, ibid. (1980) 144:710) are cultured overnight and the appropriate cultures mixed and spread on AB plates containing 150 ug/ml kanamycin. Single colonies are restreaked twice. Correct integration is verified by Southern analysis of total Agrobacterium DNA. Endonuclease digested DNA is probed with nick-translated pBrx8.

The bromoxynil specific nitrilase gene is expressed in gall tissue.

The plasmid pBrx9, which carries the nitrilase gene on a 2.6kb fragment, was digested with BamHI and treated with Bal31 to remove some 5' flanking region. BamHI linkers were added and reclosure was accomplished. The resulting plasmid which provided ampicillin resistance were transformed into *E. coli* as described previously and transformants selected on ampicillin selective medium to provide 5.2kb plasmids pBrx16 and pBrx17, which carry the nitrilase gene on a 2.6kb fragment. pBrx16 was digested with BamHI and partially digested with HincII resulting in the 1.2kb nirilase gene fragment.

The BamHI-HincII fragment ws inserted into BamHI-SmaI digested pCGN46 to provide the 6.6kb plasmid pBrx22 containing the nitrilase gene fragment.

PCGN46 (Comai et al., *Nature* (1985) 317:741-744) is a mannopine synthase (MAS) expression casette and contains a MAS promoter and ocs 3' region. Construction of pCGN46 was accomplished in the following manner. An approximately 5.5kbp EcoRI fragment (Eco13 or EcoC) carrying a portion of the T-R DNA (Barker et al., *Plant Mol. Biol.* (1983) 2:325) including the mannopine synthase promoter region ($P_{MAS}$) was cloned in a vector designated pVK232. After digestion of pVK232 with EcoRI, Eco13 was inserted into the EcoRI site of pACYC184 to yield plasmid pCGN14. pCGN14 was digested with SphI and ClaI (respectively at position 21562 and 20128 of the Barker et al. sequence, supra) to remove the $P_{MAS}$ region which was inserted into pUC19 (Pharmacia, Inc.) which had been digested with SphI and AccI to yield PCGN40. The $P_{MAS}$ region includes a ClaI recognition site internally which is methylated, so as to resist digestion.

pCGN40 was digested with EcoRV and EcoRI where the EcoRV site is in the T-DNA, while the EcoRI site is in the polylinker of pUC19 to provide a fragment having the $P_{MAS}$ region. pCGN451 containing the octopine synthase cassette was digested with SmaI and EcoRI and the larger fragment isolated from which the octopine synthase 5' region had been removed. The EcoRV-EcoRI $P_{MAS}$ region was substituted into pCGN451 for the octopine synthase 5' region, where the transcriptional initiation and termination regions were separated by a polylinker to provide pCGN46.

The palsmid pBrx22 containing the 1.2kb nitrilase gene fragment was transformed into E. coli as described previously. The plasmid was isolated in conventional ways and digested with Xho I to provide a 4.1kb fragment containing MAS promoter, bromoxynil gene containing 25 base pairs of bacterial 5' untranslated sequence and ocs 3' region. The 4.1kb fragment was inserted into the SalI-digested plasmid pCGN783 to provide the approximately 31kb plasmid pBrx28.

Construction of pCGN783
Construction of pCGN167

To construct pCGN167, the AluI fragment of CaMV (bp 7144-7735) (Gardner et al. *Nucl. Acids Res.* (1981) 9:2871-2888) was obtained by digestion with AluI and cloned into the HincII site of M13mp7 (Vieira *Gene* (1982) 19:259) to create C614. An EcoRI digest of C614 produced the EcoRI fragment from C614 containing the 35S promoter which was cloned into the EcoRI site of pUC8 (Vierra et al., *Gene* (1982) 19:259) to produce pCGN146.

To trim the promoter region, the BglII site (bp 7670) was treated with BglII and Bal31 and subsequently a BglII linker was attached to the Bal31 treated DNA to produce pCGN147.

pCGN148a containing a promoter region, selectable marker (KAN with 2 ATG's) and 3' region was prepared by digesting pCGN528 (see below) with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al. *Mol. Gen.* (1979) 177:65) with HindIII-BamHI and inserting the HindIII-BamHI fragment containing the kanamycin gene into the HindIII-BamHI sites in the tetracycline gene of pACYC184 (Chang & Cohen *J. Bacteriol.* (1978) 134,1141-1156). pCGN526 was made by inserting the BamHI fragment 19 of pTiA6 (Thomashow et al. Cell (1980) 19:729-739) into the BamHI site of PCGN525. pCGN528 was obtained by deleting the small XhoI fragment from pCGN526 by digesting with XhoI and religating.

pCGN149a was made by cloning the BamHI kanamycin gene fragment from pMB9KanXXI into the BamHI site of pCGN148a.

pMB9KanXXI is a pUC4K variant (*Vieira & Messing*, Gene (1982) 19:259:268) which has the XhoI site missing but contains a functional kanamycin gene from Tn903 to allow for efficient selection in Agrobacterium.

pCGN149a was digested with BglII and SphI. This small BglII-SphI fragment of pCGN149a was replaced with the BamHI-SphI fragment from M1 (see below) isolated by digestion with BamHI and SphI. This produces pCGN167, a construct containing a full length CaMV promoter, 1ATG-kanamycin gene, 3' end and the bacterial Tn903-type kanamycin gene. M1 is an EcoRI fragment from pCGN550 (see construction of pCGN587) and was cloned into the EcoRI cloning site of M13mp9 in such a way that the PstI site in the 1ATG-kanamycin gene was proximal to the polylinker region of M13mp9.

Construction of 709 (1ATG-Kanamycin—3' region)

pCGN566 contains the EcoRI-HindIII linker of pUC18 (Yanisch-Perron, ibid) inserted into the EcoRI-HindIII sites of pUC13-cm (*K. Buckley*, Ph.D. thesis, UC-San Diego, 1985). The HindIII-BglII fragment of pNW31c-8, 29-1 (*Thomashow et al.* (1980) *Cell* 19:729) containing ORF1 and 2 (*Barker et al.* (1983), supra) was subcloned into the HindIII-BamHI site of pCGN566 producing pCGN703.

The Sau3A fragment of pCGN703 containing the 3' region of transcript 7 from pTiA6 (corresponding to bases 2396-2920 of pT115955 (*Barker et al.* (1983), supra) was subcloned into the BamHI site of pUC18 (*Yanisch-Perron et al.* (1985), supra) producing pGN709.

Construction of pCGN766c (35s promoter—3' region)

The HindIII-BamHI fragment of pCGN167 (for construction see infra) containing the CaMV-35S promoter, 1ATG-kanamycin gene and the BamHI fragment 19 of pTiA6 was cloned into the BamHI-HindIII sites of pUC19 (Norrander et al. (1983), supra; Yanisch-Perron et al. (1985), supra) creating pCGN976.

The 35S promoter and 3' region from transcript 7 was developed by inserting a 0.7kb HindIII-EcoRI fragment of pCGN976 (35S promoter) and the 0.5kb EcoRI-SalI fragment of pCGN709 (transcript 7:3', for construction, see supra), into the HindIII-SalI sites of pCGN566 creating pCGN766c.

Final Construction of pCGN783

The 0.7kb HindIII-EcoRI fragment of pCGN766c (CaMV-35S promoter) was ligated to the 1.5kb EcoRI-SalI fragment of pCGN726c (1-ATG-KAN-3' region) into the HindIII-SalI sites of pUC119 (*J. Vieira*, Rutgers University, New Jersey) to produce pCGN778.

The 2.2kb region of pCGN778, HindIII-SalI fragment containing the CaMV 35S promoter (1-ATG-KAN-3' region) replaced the HindIII-SalI polylinker region of pGN739 to produce pCGN783.

pBrx17 was digested with BamHI and partially digested with HincII resulting in the 1.2kb nitrilase gene fragment. The bamHI—HincII fragment was inserted into BamHI—SmaI digested pCGN566 to provide the 3.7kb plasmid pBrx25 containing the nitrilase gene fragment.

pCGN566 was constructed in the following manner. pUC13 (Cm$^R$) (Ken Buckley Ph.D. thesis, U.C., San Diego) was digested with EcoRI and HindIII and polylinkers from pUC18 and pUC19 were inserted respectively into the linearized pUC13 to give pCGN566 which carries a chloramphenical resistance marker.

The plasmid pBrx25 containing the 1.2kb nitrilase gene fragment was transformed into E. coli as described previously. The plasmid was isolated in conventional ways and digested with BamHI and EcoRI to provide again the 1.2kb nitrilase gene fragment. The BamHI and EcoRI fragment was inserted into the BamHI and EcoRI digested pCGN46 to provide the 6.6kb plasmid pBrx27 containing the nitrilase gene fragment.

pBrx27 was transformed into E. coli as described previously. The plasmid was isolated in conventional ways and digested with XhoI to provide a 4.1kb fragment containing MAS promoter, bromoxynil gene containing 11 base pairs of bacterial 5' in translated sequence and ocs 3' region. The 4.1kb fragment was inserted into SalI—digested pCGN783 to provide the approximately 31kb plasmid pBrx29.

Detection of nitrilase expression

Plasmids pBrx28 and pBrx29 were transformed into the *Agrobacterium tumefaciens* strain K12. (Nester, *Ann. Rev. Micro.* (1981) 35: 531. Hoekema et al., *Nature* (1983) 303: 179) K12 (pBrx28) and K12 (pBrx29)) Kalanchoe (Garfinkel, *Bacteriol.* (1980) 144: 732).

About 1 gm (fresh weight) of gall tissue ws ground in liquid nitrogen in buffer containing 0.1M Tris pH 7.5, 10 mM EDTA, 0.15M NaCl, 0.05% NP-40, 25 mg/ml BSA, 1 mM DTT and 0.13 ug/ml leupeptin. Samples were homogenized after the addition of 0.05 g polyvinylpyrrolidone (Sigma), then centrifuged at 15,000 g for 15 min. at 4° C. 25 ul of antiserum, prepared by injecting purified nitrilase into rabbits, and 250 ul 10% (w/v) suspension of *S. aureus* (Calbiochem) were added to each supernatant and incubated for 16 hr. at 4° C. Samples were then centrifuged and the pellet washed twice with 20 mM Tris pH 7.5, 1 mM EDTA, 150 mM NaCl and 0.05% NP-40. The pellets were resuspended in 100 ul 0.125M Tris pH 6.8, 4% SDS, 20% glycerol and 10% BMe and heated for 2 min. at 90° C. The entire sample was electrophoresed on 10% acrylamide gels (Laemmli, V.K. *Nature* 227: 680–685 (1970)). The resolved polypeptides were transferred to nitrocellulose filters (Schleicher and Schuell) as described by Burnette (*Anal. Biochem.* 112: 195–203 (1981)). Nitrocellulose filters (Schleicher & Schuell) were then incubated in BLOTTO (Johnson et al, *Gen. Anal. Technol.* 1, 38–42 (1983)) for 1–3 hrs. at 42° C. followed by overnight incubation at room temperature in BLOTTO containing a 1:50 solution of anti-nitrilase serum. Filters were washed for 10 min. in 20 mM Tris pH 7.5, 150 mM NaCl; for 20 min. in the same buffer containing 0.05% Tween-20 and for another 10 min. in buffer without Tween-20. BLOTTO containing $10^6$ cpm/ml of $^{125}$I-labelled protein A (9u Ci/mg; NEN) was then added to filters and incubated at room temperature for 2 hrs. The filters were washed overnight in 50 mM Tris pH 7.5, 1M Nacl and 0.4% Sarkosyl. After rinsing and drying, filters were exposed to Kodak AR X-ray film at −70° C. using a Dupont Cronex intensifying serum.

Transformation and regeneration of tobacco leaf splices co-cultivated with *A. tumefaciens*

Tobacco plants are cultivated axenically (25° C., white light (16 hr); MS (1 mg/L IAA, 0.15 mg/L kinetin). Three-week-old plants maintained through main shoot transplant are used as tissue donors. Young leaves (down to the fourth from the top) are selected, leaf disks 2 mm in diameter are punched out and placed in Petri dishes (3 cm in diameter) in 1 ml of MS medium with 1 mg/L IAA. After keeping the disks overnight in total darkness, Agrobacterium (A772xpN1 or pN2) cells ($10^8$–$10^9$ /ml in plant culture medium) are added to these cultures. Co-cultivation is carried out for 18–24 hr in darkness. Leaf slices are freed from Agrobacterium by washing 3× with MS medium lacking hormones and containing 350 mg/L cefotaxine (Boehringer-Mannheim). Leaf splices are transferred in 9 cm Petri dishes in 10 ml of MS medium without hormones. Phytagar (Gibco, 0.6%; cefotaxine, 350 mg/L) Petri dishes are sealed with parafilm and kept under the same conditions as tissue donor plants. Regenerating shoots are visible in the following 2–5 weeks.

Plants are sprayed at the 6-leaf stage by directing a spray of bromoxynil solution toward the potted plant. Each 4" pot contains a plant and receives 2.5 ml of spray. Plants are grown in a growth chamber at 25° C., 70% relative humidity, 60 hr light period. Growth is scored 9 days after spraying by counting the new leaves longer than 0.5 cm.

Construction of a tabacco small subunit promoter-bromoxynil gene chimera for expression of bromoxynil-specific nitrilase in tobacco Construction of a tobacco ssu promoter cassette Genomic clones containing the tobacco small subunit gene were isolated from EcoRI partial genomic library prepared from *Nicotiana tabacum* (Samsum) DNA. Clones were screened using a 740 bp PstI DNA segment of a pea small subunit cDNA clone (Broglie et al., *Proc. Natl. Acad. Sc.i U.S.A.* (1981) 78:7304–7308). A 3.4Kb EcoRI fragment containing a tobacco coding region and 5'-flanking sequence was cloned from a Charon 32 lambda phage clone (3-8) into M13mp18 (Yanisch-Perron et al., *Gene* (1985) 33:103–119), which subclone was designated NSUE2018. The location of the TATA box (promoter) and putative ATG initiation codon for the small subunit protein was determined by DNA sequencing. A single-stranded DNA template was prepared from NSUE2018 and annealed to a 25 base single-strand synthetic oligomer (5'TGTTAATTACACTTTAAGACAGAAA3'). This sequence is complementary to the 25 base immediately 5' of the putative ATG of the tobacco small subunit gene. The primer was extended to produce dsDNA employing the Klenow fragment of DNA polymerase I, followed by digestion with HindIII to produce a double-stranded DNA fragment having a blunt end beginning at the primer at one end and the HindIII overhang at the other end. pUC18 was digested with SmaI and HindIII and the dsDNA fragment prepared above inserted into the polylinker to provide a 4.1Kb plasmid designated pCGN625. pCGN625 was then digested with HindIII, blunt-ended with the Klenow fragment, digested with EcoRI and inserted into EcoRI-SmaI digested pUC18 to produce a 4.1Kb plasmid pCGN627. A 6.3Kb DNA segment was obtained comprising a BamHI-PstI fragment from pACYC177 (Chang & Cohen, *J. Bacteriol.* (1978) 134:1141–1156) joined at the PstI site to a PstI-EcoRI fragment comprising ocs 3' region, bp 12823 (EcoRI) to bp 10069 (PstI) (Barker et al., *Plant Molec. Biol.* (1984) 2:335–350). The 6.3Kb DNA segment was inserted into pCGN627 digested with BamHI and EcoRI, so as to have the ocs 3' region adjacent to the tobacco ssu fragment, providing a 7.7Kb plasmid, pCGN630.

The pCGN630 plasmid was then manipulated by digesting with BamHI, blunt ending with the Klenow fragment, recircularizing, digesting with KpnI, blunt ending with T4 polymerase and insertion of BamHI linkers to provide a BamHI site. The resulting plasmid pCGN1509 was digested with BglII, blunt ended with Klenow polymerase, followed by ligation with HindIII linkers. The resulting plasmid pCGN1510 has a HindIII site internal to the ocs 3' region and a HindIII site adjacent and external to the tobacco ssu region. pCGN1510 was then digested with BamHI and SstI cutting in the region between the ssu region and the ocs 3' region and a BamHI-SstI fragment from pBrx25 inserted, so as to be between and in the correct orientation, the ssu promoter region and the ocs 3' terminator region. The resulting 8.9Kb plasmid was designated pBrx36.

pBrx36 was digested with HindIII and inserted into HindIII digested pCGN783 to provide pBrx39 and pBrx40, with the nitrilase gene in the opposite and the same direction of transcription as the kanamycin gene, respectively.

The plasmids were transformed into *A. tumefaciens* strain LBA4404, followed by co-cultivation with tobacco (*Nicotiana tabacum* cv. "Xanthi") cotyledonary explants. Kanamycin-resistant shoots were regenerated into tobacoo plants in accordance with conventional techniques.

Phenotype of Transgenic Tobacco Plants Expressing the Bromoxynil-Specific Nitrilase Gene Leaf tissue from transformed tobacco plants (5–6 leaf stage) were shown to express the nitrilase protein by conventional Western analysis. Approximately 5 mm leaf section from surface-sterilized (10% hypochloriate; water-washed) leaves were suspended in bromoxynil containing media under photoautotrophic conditions. The media employed was MS salts containing 0.93 mg/l naphthylacetic acid and 0.11 mg/l benzylaminopurine, with varying amounts of bromoxynil. The concentration of bromoxynil varied from $10^{-3}$ to $10^{-6}$M at 0.1 dilutions. The photoautotrophic conditions were 5% $CO_2$, 10% $O_2$, 85% $N_2$. Control tobacco leaf sections which had not been transformed were bleached (inhibited) at $10^{-6}$M bromoxynil. By contrast, transformed leaf sections expressing the bromoxynil-specific nitrilase from plasmids pBrx39 and pBrx40 were resistant to $10^{-5}$M and $10^{-4}$M bromoxynil, respectively.

Phenotype of Transgenic Tomato Plants Expressing the Bromoxynil-Specific Nitrilase Gene Co-cultivation of tomato (*Lycopersicon esculentum* cv. UC828) cotyledonary explants was carried out as described previously with tobacco and kanamycin shoots regenerated. Leaf tissue from transformed tomato plants (7–10 leaf stage) was shown to express the nitrilase protein by standard Western analysis. Approximately 5 mm leaf sections from surface-sterilized (10% hypochlorite; water washed) leaves were suspended in bromoxynil-containing medium at varying concentrations under photoautotrophic conditions. The media was MS salts containing 2 mg/l 2,4-dichloroacetic acid, 1 mg/l isopentyladenine and 100 mg/l myoinositol and bromoxynil at $10^{-5}$ or $10^{-6}$M. The same photoautotrophic conditions were employed as described for tobacco. Control leaf sections which had not been transformed were bleached at $10^{-6}$M bromoxynil, while transformed plants expressing the bromoxynil-specific nitrilase gene from pBrx29 were resistant to $10^{-5}$M bromoxynil. Transgenic tomato plants (10–20 leaf stage) were sprayed with a commercial formulation of bromoxynil (BUCTRIL) and found to be resistant at 0.5 lbs/acre.

Preparation of Altered Nitrilase Having a Substituted C-terminus

Plasmid Brx9 was digested with Sph1 and then recircularized so as to introduce a deletion in the coding region at the C-terminus of the nitrilase gene. The DNA sequence from pUC18 is in reading frame with the 3'-Sph1 site of the nitrilase coding region, adding about ten codons to a TGA codon from pUC18.

The presence of the additional 10 codons is adventitious and supports the fact that these codons may be removed to produce a truncated nitrilase, without significantly affecting the activity of the nitrilase.

The following is the sequence with the predicted amino acids of the C-terminal modified nitrilase (nit-11).

| Pos | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
|  | ATG Met | GCC Ala | ACC Thr | ACT Thr | TTC Phe | AAA Lys | GCA Ala | GCC Ala | 92 GCT Ala | GTT Val | CAG Gln | GCC Ala | GAA Glu | CCG Pro | GTA Val | TGG Trp | ATG Met | 119 GAT Asp |
|  | GAC Asp | GCT Ala | ATG Met | ACA Thr | GCC Ala | AAG Lys | GAT Asp | ACC Thr | 146 GTG Val | ACG Thr | CTA Leu | GTA Val | GCT Ala | AAA Lys | GCA Ala | TGG Trp | GCA Ala | 173 GCT Ala |
|  | GGC Gly | GCG Ala | GCG Ala | CTC Leu | GTC Val | GCA Ala | TTT Phe | CAG Gln | 200 GAA Glu | TTG Leu | TGG Trp | ATT Ile | CCG Pro | GGG Gly | TAC Tyr | CCA Pro | GGA Gly | 227 TCC Phe |
|  | ATG Met | CTC Leu | ATC Ile | CAC His | AAC Asn | ACC Thr | CCC Pro | GAA Glu | 254 ACC Thr | CTA Leu | CCA Pro | TTC Phe | ATC Ile | ATT Ile | TAC Tyr | CCA Pro | GGA Gly | 281 AAG Lys |
|  | CAG Gln | GCA Ala | ACG Thr | GCC Ala | GCC Ala | CAA Gln | GGA Gly | AGC Ser | 308 GAA Glu | ATC Ile | CCA Pro | AAA Lys | ATT Ile | GGC Gly | TAC Tyr | GAA Glu | CGC Arg | 335 CAG Gln |
|  | GAG Glu | CAT His | ATT Ile | GCC Ala | ATG Met | GAT Asp | TTT Phe | CTC Leu | 362 GGG Gly | TAC Tyr | AGC Ser | TTT Phe | CGG Arg | ATT Ile | TGC Cys | AGC Ser | GCT Ala | 389 CTC Leu |
|  | TAC Tyr | TTA Leu | CAA Gln | CAA Gln | GCG Ala | CTC Leu | CTT Leu | CGC Arg | 416 GCC Ala | GAT Asp | GGC Gly | ACT Thr | GCT Ala | CGG Arg | GGC Gly | AAC Asn | CGT Arg | 443 CGA Arg |
|  | AAG Lys | AAT Asn | TCA Ser | AAA Lys | CAA Gln | CTA Leu | CTT Leu | AAC Asn | 470 CGA Arg | GGT Gly | CTT Leu | AAG Lys | ATC Ile | ACC Thr | ATT Ile | CGT Arg | TAC Tyr | 497 TCG Ser |
|  | GAC Asp | ATC Ile | CAG Gln | ACG Thr | ATG Met | GAT Asp | TTT Phe | ACT Thr | 524 GTT Val | AGC Ser | GGC Gly | TTT Phe | GTG Val | GCT Ala | GGA Gly | TGC Cys | CAG Gln | 551 GCG Ala |
|  | GAG Glu | CTC Leu | CTC Leu | GCC Ala | ACC Thr | CAG Gln | AAG Lys | GAG Glu | 578 TTT Phe | GCG Ala | CTC Leu | GCT Ala | CCT Pro | GGT Gly | CTC Leu | GAC Asp | AAC Asn | 605 ATA Ile |
|  | CAT His | ACG Thr | GCC Ala | ATC Ile | TCC Ser | ACG Thr | TAC Tyr | TAC Try | 632 CTT Leu | AGC Ser | CCA Pro | CAG Gln | ACG Thr | GGC Gly | GGT Gly | GAG Glu | CAG Gln | 659 TCC Ser |
|  | ATC Ile | GGC Gly | ATC Ile | AAC Asn | TGG Trp | ACC Thr | ACC Thr | AAC Asn | 686 GCA Ala | GGA Gly | GCC Ala | GAG Glu | TTC Phe | GTC Val | GCG Ala | GAA Glu | CTC Leu | 713 ATG Met |
|  | TCG Ser | ACG Thr | GCC Ala | GTG Val | GTT Val | CAG Gln | CCG Pro | GTC Val | 740 GGC Gly | GCC Ala | ATC Ile | ACG Thr | GCA Ala | TTC Phe | ATC Ile | GTT Val | GAC Asp | 767 AGG Arg |
|  | TCA | AAC | CCG | AAT | CAG | TAT | GGT | ACC Thr | 794 GGT | CTT | GCG | GCA | ATC | TAC | GGG | CCT | CGG | 821 GAC |

| | | | | | | | | -continued | | | | | | | |
|---|---|---|---|---|---|---|---|---|---|---|---|---|---|---|---|
| Tyr | Asn | Pro | Asn | Gln | Tyr | Leu | Gly | Gly | Tyr | Ala | Arg | Ile | Tyr | Gly | Asp |
| ATG MET | CAG Gln | TTG Leu | AAG Lys | AGC Ser | AAG Lys | TCG Ser | TTG Leu | 848 TCA Ser | ACC Thr | GAA Glu | GAG Glu | GGC Gly | ATC Ile | GTC Val | 875 GCC Ala |
| GAG Glu | ATC Ile | GAC Asp | CTG Leu | TCG Ser | ATG MET | CTT Leu | GAG Glu | 902 GCA Ala | AAG Lys | TAC Tyr | TCG Ser | CTC Leu | GAT Asp | CCC Pro | 929 GGC Gly |
| CAC His | TAT Tyr | TCG Ser | CGC Arg | CCT Pro | GAT Asp | GTG Val | TTC Phe | 956 AGC Ser | TCG Ser | ATT Ile | AAC Asn | CGG Arg | CAA Gln | CGG Arg | 983 CCT Pro |
| GCG Ala | GTG Val | TCA Ser | GAA Glu | GTT Val | ATC Ile | GAC Asp | TCA Ser | 1010 AAC Asn | GAC Asp | GAG Glu | GAC Asp | CCG Pro | AGA Arg | GCA Ala | 1037 TGC Cys |
| AAG Lys | CTT Leu | GGC Gly | ACT Thr | GGC Gly | CGT Arg | TTT Phe | ACA Thr | 1064 ACG Thr | TGA | CTG Leu | GGA Gly | AAA Lys | CCC Pro | TGG Trp | 1091 TAC Tyr |
| TTA Leu | CAG Gln | GTC Val | GCC Ala | GTT Val | ACT Thr | AGC Ser | GTT Val | 513 GGT Gly | GTG Val | GGT Gly | GCC Ala | CTC Leu | AAC Asn | GCA Ala | 540 GAG Glu |
| AAT Asn | TTG Leu | CAG Gln | TCG Ser | TGG Trp | AAC Asn | AAG Lys | TTT Phe | 567 GCG Ala | GCT Ala | GCG Ala | GTG Val | GGT Gly | CCC Pro | TGG Trp | 594 CAT His |
| ATC Ile | TCC Ser | GCC Ala | ATC Ile | AAC Asn | GTC Val | ACG Thr | CTT Leu | 621 GGA Gly | CCT Pro | GCG Ala | GCC Ala | TTC Phe | AAC Asn | TGC Cys | 648 ATC Ile |
| GGC Gly | GCC Ala | ATC Ile | GTG Val | CAG Gln | CCG Pro | TAC Tyr | AGC Ser | 675 GCC Ala | ACG Thr | ACG Thr | TTC Phe | ATC Ile | GGA Gly | CAG Gln | 702 TCG Ser |
| ACG Thr | CAG Gln | GTG Val | CCG Pro | GGA Gly | CTT Leu | ACC Thr | GGC Gly | 729 ATC Ile | GCC Ala | GCC Ala | CGG Arg | TTC Phe | GGT Gly | CTC Leu | 756 TAC Tyr |
| AAC Asn | CCG Pro | AAT Asn | CAG Gln | TAT Tyr | CTT Leu | TAC Tyr | GGT Gly | 783 GGG Gly | TAC Tyr | GCA Ala | TTC Phe | ATC Ile | GAA Glu | GAC Asp | 810 ATG MET |
| CAG Gln | TTG Leu | AAG Lys | AGC Ser | AAG Lys | TCG Ser | ACC Thy | TCA Ser | 837 CCG Pro | ACC Thr | GAA Glu | CGG Arg | TAC Tyr | GGG Gly | CCT Pro | 864 GAG Glu |
| ATC Ile | GAC Asp | CTG Leu | TCG Ser | ATG MET | CTT Leu | GAG Glu | GCA Ala | 891 GCA Ala | AAG Lys | TAC Tyr | TCG Ser | CTC Leu | CCC Pro | ACG Thr | 918 CAC His |

-continued

| | | | | | | | | Pos | | | | | | | | | | Pos | |
|---|---|---|---|---|---|---|---|---|---|---|---|---|---|---|---|---|---|---|---|
| TAT Tyr | TCG Ser | CGC Arg | CCT Pro | GAT Asp | GTG Val | TTC Phe | AGC Ser | 945 GTG Val | TCG Ser | ATT Ile | AAC Asn | CGG Arg | CAA Gln | CGG Arg | CAG Gln | CCT Pro | 972 GCG Ala |
| GTG Val | TCA Ser | GAA Glu | GTT Val | ATC Ile | GAC Asp | TCA Ser | AAC Asn | 999 GGT Gly | GAC Asp | GAG Glu | GAC Asp | CCG Pro | AGA Arg | GCA Ala | GCA Ala | TGC Cys | 1026 GAG Glu |
| CCC Pro | GAC Asp | GAG Glu | GGG Gly | GAT Asp | CGT Arg | GAG Glu | GTC Val | 1053 GTA Val | ATC Ile | TCT Ser | ACG Thr | GCA Ala | ATA Ile | GGG Gly | GTT Val | CTA Leu | 1080 CCC Pro |
| CGT Arg | TAT Tyr | TGC Cys | GGA Gly | CAT His | TCC Ser | TAA | TAA | 1107 AAA Lys | GAG Glu | ACA Thr | CGT Arg | TGT Cys | ACC Thr | AAA Lys | GGG Gly | GTG Val | 1134 TTC Phe |
| ATG MET | TCC Ser | AGA Arg | CGC Arg | AGA Arg | AAA Lys | TAT Try | AGC Ser | 1161 CCA Pro | GAG Glu | TTA Leu | AAA Lys | CGC Arg | GAA Glu | GCC Ala | ATC Ile | GCT Ala | 1188 TTA Leu |
| ACC Thr | CGT Arg | C His | | | | | | 1215 | | | | | | | | | |

Preparation of Modified Nitrilase Having N-Terminal Substitution

Plasmid pBrx9 was digested with BamH1, followed by resection with Bal31 for about 5 min to remove about 51 nt. The enzyme was inactivated, the resected linear DNA sequence ligated with BamH1 linkers, digested with BamH1 and recircularized under ligating conditions. The resulting plasmid pBrx15 was about 5.1 kb and had a small number of the codons at the 5'-terminus deleted. pBrx15 was partially digested with HincI, so as to cleave at the Hinc site downstream from the coding region for the nitrilase and completely digested with BamH1 to provide a fragment which had the coding region for the nitrilase truncated at the 5'-terminus. This fragment was inserted into pCGN 566 which had been completely digested with BamH1 and SmaI to produce plasmid pBrx23, of 3.7Kb. Plasmid pCGN 566 is a derivative of pUC13 with polylinkers from pUC18 and pUC19 and the chloramphenicol resistance gene. The fragment from pBrx15 is inserted to be in reading frame with an upstream initiation codon and where 17 amino acids encoded by the pUC19 sequence replace amino acids of the naturally occurring nitrilase.

Based on the above sequence, the nitrilase retains activity with an extended N-terminal amino acid sequence as well as being truncated at the N-terminal sequence, or substituting the naturally occurring amino acids of the N-terminal sequence for other amino acids.

The following provides the sequence of the N-terminal modified nitrilase (nit-23).

| | | | | | | | | | |
|---|---|---|---|---|---|---|---|---|---|
| ATG MET | ACC Thr | ATG MET | ATT Ile | ACG Thr | CCA Pro | AGC Ser | TTG Leu | GCC Ala | 27 CAT His |
| GAC Asp | ACT Thr | ACA Thr | TTC Phe | AAA Lys | GCC Ala | GAA Glu | CAG Gln | TGC Cys | 54 CCG Pro |
| GCT Ala | GCA Ala | GCA Ala | GCC Ala | GAT Asp | GCC Ala | GCT Ala | CTA Leu | GTA Val | 81 GTT Val |
| GCG Ala | CAG Gln | ACG Thr | CTC Leu | GTG Val | GCA Ala | CCG Pro | TGG Trp | GCC Ala | 108 GCC Ala |
| CTC Leu | ACG Thr | CTC Leu | GCC Ala | AAC Asn | CAA Gln | ACC Thr | GAA Glu | CCA Pro | 135 ACG Thr |
| GCA Ala | ATC Ile | CAC His | ATT Ile | GGA Gly | GAT Asp | CCC Pro | CTA Leu | ATT Ile | 189 TTG Leu |
| CAT His | AAC Asn | GCC Ala | CAA Gln | CCA Pro | CAA Gln | GAA Glu | GAA Glu | TTC Phe | 243 CTA Leu |
| ATG MET | TCA Ser | ATT Ile | CAA Gln | CCA Pro | GAT Asp | CCA Pro | AGC Ser | AAA Lys | 297 ATC Ile |
| CTC Leu | AAA Lys | ATG MET | CCA Pro | GTC Val | CTC Leu | TTT Phe | GGC Gly | GAA Glu | 351 TAC Tyr |
| TTA Leu | CAG Gln | ACC Thr | TCG Ser | CAG Gln | CGG Arg | ACT Thr | CTC Leu | ATC Ile | 405 GAT Asp |
| AAT Asn | TTG Leu | GCC Ala | TGG Trp | GCC Ala | CTT Leu | AAC Asn | AGC Ser | TTT Phe | 459 GAA Glu |
| ATC Ile | TCC Ser | TCG Ser | AAC Asn | TAC Tyr | CCA Pro | TTC Phe | GAG Glu | GTG Val | 513 GGT Gly |
| GGC Gly | GCC Ala | TGG Trp | AAC Asn | TAC Tyr | CAG Gln | GTC Val | GCC Ala | CCT Pro | 567 GCG Ala |
| ACG | GTG | AAC Asn | TAC Tyr | ACG Thr | CAG Gln | GTT | ACG Thr | ACG Thr | 621 GGA Gly |

Sequence positions: 27, 54, 81, 108, 135, 162, 189, 216, 243, 270, 297, 324, 351, 378, 405, 432, 459, 486, 513, 540, 567, 594, 621, 648, 675, 702, 729, 756

End codons at marked positions:
- 27 CAT His
- 54 CCG Pro
- 81 GTT Val
- 108 GCC Ala
- 135 ACG Thr
- 162 GGC Gly
- 189 TTG Leu
- 216 ATG MET
- 243 CTA Leu
- 270 CAG Gln
- 297 ATC Ile
- 324 GAG Glu
- 351 TAC Tyr
- 378 TAC Tyr
- 405 GAT Asp
- 432 AAG Lys
- 459 GAA Glu
- 486 GAC Asp
- 513 GGT Gly
- 540 GAG Glu
- 567 GCG Ala
- 594 CAT His
- 621 GGA Gly
- 648 ATC Ile
- 675 GCC Ala
- 702 TCG Ser
- 729 ATC
- 756 TAC

| Pos | | | | | | | | | Pos | | | | | | | | |
|---|---|---|---|---|---|---|---|---|---|---|---|---|---|---|---|---|---|
| | Thr | Gln | Val | Val | Gly | Pro | Thr | Gly | Ile | Ala | Phe | Glu | Ile | Glu | Asp | Arg | Tyr |
| 783 | AAC Asn | CCG Pro | AAT Asn | CAG Gln | TAT Tyr | CTT Leu | GGT Gly | GGT Gly | GGG Gly | GCG Ala | CGG Arg | ATC Ile | TAC Tyr | GGG Gly | CCT Pro | GAC Asp | 810 ATG MET |
| 837 | CAG Gln | TTG Leu | AAG Lys | AGC Ser | AAG Lys | TCG Ser | TTG Leu | TCA Ser | CCG Pro | GAA Glu | GAG Glu | GGC Gly | ATC Ile | GTC Val | TAC Tyr | GCC Ala | 864 GAG Glu |
| 891 | ATC Ile | GAC Asp | CTG Leu | TCG Ser | ATG MET | CTT Leu | GAG Glu | GCA Ala | GCA Ala | TAC Tyr | TCG Ser | CTC Leu | GAT Asp | CCC Pro | ACG Thr | GGC Gly | 918 CAC His |
| 945 | TAT Tyr | TCG Ser | CGC Arg | CCT Pro | GAT Asp | GTG Val | TTC Phe | AGC Ser | GTG Val | ATT Ile | AAC Asn | CGG Arg | CAA Gln | CGG Arg | CAG Gln | CCT Pro | 972 GCG Ala |
| 999 | GTG Val | TCA Ser | GAA Glu | GTT Val | ATC Ile | GAC Asp | TCA Ser | AAC Asn | GGT Gly | GAG Glu | GAC Asp | CCG Pro | AGA Arg | GCA Ala | GCA Ala | TGC Cys | 1026 GAG Glu |
| 1053 | CCC Pro | GAC Asp | GAG Glu | GGG Gly | GAT Asp | CGT Arg | GAG Glu | GTC Val | GTA Val | TCT Ser | ACG Thr | GCA Ala | ATA Ile | GGG Gly | GTT Val | GTA Leu | 1080 CCC Pro |
| 1107 | CGT Arg | TAT Tyr | TGC Cys | GGA Gly | CAT His | TCC Ser | TAA | TAA | AAA Lys | ACA Thr | CGT Arg | TGT Cys | ACC Thr | AAA Lys | GGG Gly | GTG Val | 1134 TTC Phe |
| 1161 | ATG MET | TCC Ser | AGA Arg | CGC Arg | AGA Arg | AAA Lys | TAT Tyr | AGC Ser | CCA Pro | TTA Leu | AAA Lys | CGC Arg | GAA Glu | GCC Ala | ATC Ile | GCT Ala | 1188 TTA Leu |
| 1215 | ACC Thr | CGT Arg | C His | | | | | | | | | | | | | | |

Purification of the Wild-Type and Altered Nitrilase

Nitrilase was prepared from stationary phase MM 294 *E. coli* cells containing the pBrx9, pBrx11 or pBrx28 plasmids. Cultures were grown under ampicillin selection until the whole cell nitrilase assay yielded an OD640 of approximately 2.0. Cultures were centrifuged at 8,000 xg for 15 min at 4° C. The cells were washed in 0.1M potassium phosphate buffer pH 7.4, repelleted, dried, and frozen at −20° C. The pellet was thawed at 4° C. and resuspended in 40 ml 50 mM potassium phosphate buffer with 1 mM dithiothreitol, 0.1 mM EDTA (KDE). The cell suspension was then passed through a French Pressure cell and centrifuged at 60,000 xg for 40 min at 4° C. The resulting supernatant (crude extract) was diluted with KDE buffer to a protein concentration of 12 mg/ml (Fraction I). Ammonium sulfate cuts were performed on the crude extract and the 25–35% cut (Fraction II) found to contain 85% of the nitrilase activity. This fraction was resuspended in 10 ml of KDE buffer and dialyzed extensively against this same buffer.

Fraction II was further purified over a DEAE Sephadex A-50 column (4.9cm²×40 cm) equilibratred in KDE buffer. The nitrilase peak was eluted by a 0.1M to 0.4M NaCl gradient in KDE buffer. Active fractions were pooled (Fraction III), ammonium sulfate precipitated and dialyzed into 25 mM histidine, pH 6.2. A Pharmacia chromatofocusing column (1.75 cm²×20 cm) was prepared with PBE 94 equilibrated with 25 mM histidine pH 6.2 The column was washed first with polybuffer 74 pH 4.0 to create a 6 to 4 pH gradient and the enzyme eluted with 1M NaCl. The peak containing the active enzyme fractions were ammonium sulfate precipitated and dialyzed into KDE (Fraction IV). SDS-PAGE on an 11.25% gel revealed a strong band at approximately 37,000, with a slight contaminant at approximately 70,000 molecular weight. Densitometer scanning indicated that the Fraction IV nitrilase preparation was 99% homogeneous.

The following table indicates the results of the purification and the characteristics of the purified nitrilase products.

Comparison of the Purification and Properties of The Wild-Type and Altered Bromoxynil-specific Nitrilases

| nit-wt | nit-11 | nit-23 | |
|---|---|---|---|
| Ammonium sulfate cut | 25–35% | 10–25% | 20–35% |
| DEAE Sephadex elution | 270 mM | 150 mM | 290 mM |
| Chromatofocusing elution pH 6-4 gradient/1 M NaCl wash | 1 M NaCl | pH 4.6 | 1 M NaCl |
| Specific activity | 25.7 | 55 | 19.7 |
| Fold purification | 10.3 | 16.4 | 35.8 |
| Km (mM) | 0.31 | 0.05 | 0.11 |
| Vmax (umol/min/mg) | 15 | 36 | 9 |
| Active enzyme form | dimer | multimer | dimer |

By following the above procedures, plants can be obtained which are bromoxynil resistant and can be used in the field in the presence of bromoxynil without significant adverse effect on their growth.

The subject invention provides for the improvement of plants by making them herbicidal resistant, particularly to specific benzonitrile herbicides. Thus, the gene encoding for the nitrilase may be introduced into a plant host, whereby the gene will be expressed and impart benzonitrile resistance to the plant. In addition, the enzyme can be produced by cloning of the gene in a convenient bacterial host, whereby the enzyme is expressed. Enzymes having activity which can be monitored find a wide variety of uses, in assays for various analytes or for the benzonitrile substrate. In addition, the enzymes and bacteria expressing the enzymes can be used for removing the benzonitrile herbicide from contaminated environments.

Although the foregoing invention has been described in some detail by way of illustration and example for purposes of clarity of understanding, it will be obvious that certain changes and modifications may be practiced within the scope of the appended claims.

What is claimed is:

1. A composition substantially free of bacterial cellular components comprising a bacterial nitrilase of about 34KDal molecular weight substantially specific for 3,5-dihalogenated-p-hydroxybenzonitrile and having a specific activity of at least about 0.1 umol NH$_3$/min/mg protein with bromoxynil as substrate.

2. A composition according to claim 1, wherein said bacterial nitrilase has a specific activity of at least about 0.5 umol NH$_3$/min/mg protein.

3. A composition according to claim 1, wherein said composition has a specific activity of at least about 0.1 umol NH$_3$/min/mg protein with bromoxynil as substrate.

4. A substantially pure bacterial nitrilase of about 34KDal molecular weight substantially specific for 3,5-dihalogenated-p-hydroxybenzonitrile and having a specific activity of at least about 0.1 umol NH$_3$/min/mg protein with bromoxynil as substrate.

5. A substantially pure bacterial nitrilase according to claim 1, wherein said bacterial nitrilase has a specific activity of at least about 0.5 umol NH$_3$/min/mg/-protein.

6. A substantially pure bacterial nitrilase according to claim 1, wherein said bacterial nitrilase is a nitrilase from Klebsiella.

7. A substantially pure modified bacterial nitrilase of about 34KDal molecular weight substantially specific for 3,5-dihalogenated-p-hydroxybenzonitrile and having a specific activity of at least about 0.1 umol NH$_3$/min/mg protein with bromoxynil as substrate, wherein said bacterial nitrilase is modified by at least one of substitutions, truncation or extension consisting of a total of not more than about 50 amino acids.

8. A bacterial host having a foreign gene expressing a nitrilase specific for 3,5-dihalogenated-p-hydroxybenzonitrile.

9. A bacterial host according to claim 8, wherein said bacterial host is *E. coli*.

10. An expression cassette comprising in the direction of transcription, a transcriptional and translational initiation regulatory region functional in a plant cell and a gene encoding nirilase substantially specific for 3,5-dihalogenated-p-hydroxybenzonitrile and having a specific activity of at least about 0.1 umol NH$_3$/min/mg protein with bromoxynil as substrate.

11. An expression cassette according to claim 10, wherein said cassette further comprises the right T-DNA border.

12. An expression cassette according to claim 10, wherein said transcriptional and translational initiation regulatory region is functional in a plant cell.

13. An expression cassette according to claim 12, wherein said transcriptional and translational initiation regulatory region is the regulatory region for transcription of an opine.

14. A plasmid capable of stable maintenance in at least one of *E. coli* or *A. tumefaciens* comprising an expression cassette comprising in the direction of transcription, a transcriptional and translational initiation regulatory region functional in a plant cell and a gene encoding nitrilase substantially specific for 3,5-dihalogenated-p-hydroxybenzonitrile and having a specific activity of at least about 0.1 umol $NH_3$/min/mg protein with bromoxynil as substrate.

15. A plasmid according to claim 14, wherein said expression cassette comprises the right T-DNA border.

16. A plasmid according to claim 14, wherein said transcriptional and translational initiation regulatory region is functional in a plant cell.

17. A plasmid according to claim 16, wherein said transcriptional and translational initiation regulatory region is an opine region.

18. A plasmid according to claim 17, wherein said transcriptional initiation regulatory region is the mannopine synthase initiation regulatory region.

19. A DNA sequence comprising an open reading frame coding for a nitrilase substantially specific for 3,5-dihalogenated-p-hydroxybenzonitrile and having a specific activity of at least about 0.1 umol $NH_3$/min/mg protein with bromoxynil as substrate joined at either the 5' or 3' terminus to other than the wild type DNA.

20. A DNA sequence according to claim 19, wherein said open reading frame is bacterial DNA.

21. A DNA sequence according to claim 20, wherein said bacterial DNA is Klebsiella DNA.

22. A plant cell comprising an expression cassette according to any of claims 10 to 13.

23. A plant part comprising a plant cell according to claim 22.

24. A plant comprising a plant cell according to claim 22.

25. A method for producing a nitrilase specific for a 3,5-dihalogenated-p-hydroxybenzonitrile which comprises:
isolating *K. ozaenae* which produces nitrilase specific for said 3,5-dihalogenated-p-hydroxybenzonitrile;
growing said *K. ozaenae* in an appropriate medium; and
lysing said *K. ozaenae* and isolating said nitrilase.

* * * * *